United States Patent
Groen et al.

(10) Patent No.: US 11,221,337 B2
(45) Date of Patent: Jan. 11, 2022

(54) METHOD AND TEST KIT FOR THE QUANTITATIVE DETERMINATION OF BIOMARKERS IN FECAL SAMPLES

(71) Applicants: IMMUNDIAGNOSTIK AG, Bensheim (DE); Hans-Juergen Groen, Bensheim (DE); Franz-Paul Armbruster, Bensheim (DE)

(72) Inventors: Hans-Juergen Groen, Bensheim (DE); Franz-Paul Armbruster, Bensheim (DE)

(73) Assignees: IMMUNDIAGNOSTIK AG, Bensheim (DE); Hans-Juergen Groen, Bensheim (DE); Franz-Paul Armbruster, Bensheim (DE)

( * ) Notice: Subject to any disclaimer, the term of this patent is extended or adjusted under 35 U.S.C. 154(b) by 240 days.

(21) Appl. No.: 16/613,103

(22) PCT Filed: May 11, 2018

(86) PCT No.: PCT/EP2018/062222
§ 371 (c)(1),
(2) Date: Feb. 11, 2020

(87) PCT Pub. No.: WO2018/206772
PCT Pub. Date: Nov. 15, 2018

(65) Prior Publication Data
US 2020/0209252 A1 Jul. 2, 2020

(30) Foreign Application Priority Data
May 11, 2017 (DE) .................. 10 2017 110294.9

(51) Int. Cl.
*G01N 33/68* (2006.01)
*A61B 10/00* (2006.01)
(Continued)

(52) U.S. Cl.
CPC ..... *G01N 33/6803* (2013.01); *A61B 10/0038* (2013.01); *G01N 1/405* (2013.01);
(Continued)

(58) Field of Classification Search
CPC .. G01N 33/6803; G01N 1/405; G01N 1/4055; G01N 33/721; G01N 2333/805;
(Continued)

(56) References Cited

U.S. PATENT DOCUMENTS

2011/0244461 A1* 10/2011 Tanigami ............. C12Q 1/6806
435/6.11

FOREIGN PATENT DOCUMENTS

| JP | 2003-14768 A | 1/2003 |
| JP | 2003-194825 A | 7/2003 |
| JP | 6077763 B2 | 2/2017 |

OTHER PUBLICATIONS

Edwards, "Improving Fecal Blood Testing." Gastroenterology, vol. 114, Jan. 1998, pp. 226-227, XP5138351.

* cited by examiner

*Primary Examiner* — Jennifer Wecker
*Assistant Examiner* — Michael Paul Shimek
(74) *Attorney, Agent, or Firm* — Birch, Stewart, Kolasch & Birch, LLP (57) ABSTRACT

A method comprising the steps of: (a) collecting a stool sample with the analyte and transferring a defined amount of stool sample into a prepared vessel having a sieve filter and a predetermined amount of extraction solution; (b) suspending and extracting the stool sample in the extraction solution so that the analyte goes into solution; (c) filtering the extraction solution through the sieve filter and transferring a defined amount of extraction solution to a cellulosic fibrous web having predetermined absorbency; (d) rapid drying of the extraction solution on the cellulose fibrous web at
(Continued)

ambient temperature by the capillary action of the fibrous web, wherein the fibrous web with the sample extraction solution represents a storage and transport form stable over days and weeks, on which analyte and digestive enzymes are physically separated from each other; (e) collecting and extracting the analyte from the fibrous web in a predetermined amount of assay buffer; (f) separating the fibrous web from the assay buffer with the analyte; and (g) quantitatively or qualitatively determining the analyte in the assay buffer.

12 Claims, 3 Drawing Sheets

(51) Int. Cl.
*G01N 1/40* (2006.01)
*G01N 33/72* (2006.01)
(52) U.S. Cl.
CPC ......... *G01N 1/4055* (2013.01); *G01N 33/721* (2013.01); *G01N 2333/805* (2013.01); *G01N 2333/966* (2013.01)
(58) Field of Classification Search
CPC .............. G01N 2333/966; G01N 33/48; A61B 10/0038
See application file for complete search history.

METHOD AND TEST KIT FOR THE QUANTITATIVE DETERMINATION OF BIOMARKERS IN FECAL SAMPLES

CROSS-REFERENCE TO RELATED APPLICATIONS

This application is the National Phase of PCT International Application No. PCT/EP2018/062222, filed May 11, 2018, claiming priority of earlier filed German Patent Application No. 102017110294.9, filed on May 11, 2017.

TECHNICAL FIELD

The invention concerns methods for the quantitative determination of bio-markers in fecal samples and a kit of parts therefor.

BACKGROUND OF THE INVENTION

The clinical examination of intestinal excrements is not popular. Firstly, the medical practitioner cannot immediately take the sample but has to wait until a bowel movement of the patient. Feces is further unhygienic, odour-intensive and disgusting. Thus, a device is handed out to the patient so that he himself can transfer something from his stool into an examination vessel. This is typically a non-controlled step. The fecal sample must further be weighed or sized by volume for quantitative determinations. Fecal samples are not homogeneous but their matrix consistencies and compositions depend on the food and state of health. Moreover, the target proteins for diagnostics are not stable. Intestinal bacteria and digestive enzymes are active in the intestine and thereafter after excretion. They do not only attack the target proteins but also interfere with the enzymatic or immunological determination.

Fecal samples are therefore generally frozen until examination. The freezing and thawing of stools is associated with standing times during which degradation and decomposition continue. Stabilizing buffers are also available for small quantities. The disadvantage of this is that digestion processes are difficult to inhibit and stabilisation in a buffer must be good for at least five to seven days at ambient temperatures, as long as it takes between sampling and examination in the laboratory. The analyte in the stabilisation buffer must generally survive 5 to 7 days until analysis without refrigeration, the preanalytics period will include weekends, public holidays and long transport, taking into account the warm season and extreme transport conditions.

Finally, the analytes must be extracted from the stool matrix and dissolved. If a chaotropic buffer is used for extraction the chaotropic salts must be removed prior to immunological determination so that the proteinaceous target analyte can renaturate again. Occult blood or haemoglobin are usually degraded in conventional buffer systems at a rate of 6 to 7 percent per day (Grazzini et al, *Influence of seasonal variations in ambient temperatures on performance of immunochemical faecal occult blood test for colorectal cancer screening: observational study from the Florence district*, Gut (2010), 59(11): 1511-5; Van Room et al, *Are fecal immunochemical test characteristics influenced by sample return time? A population-based colorectal cancer screening trial*. The American J. of Gastroenterology (2012) 107:99-107).

Dried stool samples are also preserved and stored on paper supports (Whatman FTA® or FTA® Card) (Nechvatal J M et al in Fecal collection, ambient preservation, and DNA extraction for PCR amplification of bacterial and human markers from human faeces, J Microbiol Methods. (2008) 72(2):124-32; Chu D M, et al., Detection of *Cyclospora cayetanensis* in animal fecal isolates from Nepal using an FTA filter-base polymerase chain reaction method. Am J Trop Med Hyg. (2004) 71(4):373-9; Subrungniang I, et al., Evaluation of DNA extraction and PCR methods for detection of *Enterocytozoon bieneusi* in stool specimens J Clin Microbiol. (2004) 42(8):3490-4). WO2016014822 (GE Healthcare) claims carriers of a fibrous material such as cellulose, glass fiber or microfibers. Further used are porous membranes of polyester, polyethersulfone (PES), polyamide (nylon), polypropylene, polytetrafluoroethylene (PTFE), polycarbonates, cellulose nitrate, cellulose acetate, or alginate. The fecal sample is sometimes treated with chaotropic and denaturing substances during drying on the carrier; see EP1109899 (Whatman PLC). However, the analyte in those dried stool samples is generally a nucleic acid, often analysed e.g. by a polymerase chain reaction (PCR). Proteins are not open to quantitative determination because they denature and can irreversibly bind to the carrier via hydrophobic interactions. A differentiating quantitative analysis is no longer possible, if at all, using simple techniques.

Consequently, there is a need for a preanalytical method by which a fecal sample is prepared and preserved for subsequent chemical protein analysis. The state of the art represents the problem.

BRIEF DESCRIPTION OF THE INVENTION

This application discloses a method as claimed in claim 1 and related test kits and reagent sets for the examination of stool samples are a further aspect of the invention. Preferred embodiments have been described in the subclaims and examples.

The pre-analytical method for preparation of fecal samples (feces, excrement, cloaca or stool) comprises the steps: (a) collecting and transferring a known amount of sample matrix into a vessel containing a known amount of aqueous protein extraction solution; (b) extracting the proteinaceous analyte from the matrix of the sample; (c) applying a known volume of aqueous extract to a carrier material having capillary and chromatographic flow properties such that the aqueous extract with the target proteins spreads on the carrier material; (d) drying the carrier material, wherein the carrier with the dried extract represents a preservation and transport form of the fecal sample. For subsequent quantitative determination of the amino acid-containing or proteinaceous fecal analyte: (e) elution of the analyte from the carrier material into a known amount of assay buffer; (f) optionally separation of the carrier material from the assay buffer and (g) quantitative determination of the proteinaceous analyte by an enzymatic or immunological reaction. The above aqueous sample extraction solution contains in molar excess relative to proteins and amino acids, preferably 1 to 50 mM/L of a ketocarboxylic acid having 1 to 12 carbon atoms, which can form water-soluble hydrated salts, when dried, with amino acids and proteins in the extract, as well as buffer salts for obtaining a pH between 3 and 10, and optionally detergents, solubilizing agents, complexing agents, redox agents, biocides, adjuvants and salts for the adjustment of ionic strength.

The ketocarboxylic acids may be selected from the group consisting of α-keto monocarboxylic acids, α-keto dicarboxylic acids, ß-keto carboxylic acids, ß-keto dicarboxylic acids, α-keto propionic acid (pyruvic acid), acetoacetic acid, ketomalonic acid (mesoxalic acid), oxaloacetic acid, oxal succinic acid, α-keto glutaric acid, isocitrate, oxohexanoic acid (ketocaproic acid), oxoheptanoic acid (ketoenanthic acid), γ-keto carboxylic acids, levulinic acid, phenylpyruvic acid, ketone derivatives and esters of terephthalic acid, and mono- or diesters of the above-mentioned ketocarboxylic acids with a linear or branched alcohol having 1 to 6 carbon atoms, glyoxylic acid, glyoxylic acid ethyl ester, pyruvic acid ethyl ester.

The extraction buffer may contain 0.001 to 5.0% by weight, based on the total weight, preferably 0.005 to 0.5% by weight, of a sugar and/or an amino sugar, preferably a preservative mono-, di- or trisaccharide, preferably sucrose, lactose, maltose or trehalose. The amino sugar may be glucosamine, N-methyl glucosamine, galactosamine or neuraminic acid. Sugars such as sucrose or dextrose are not excluded. Trehalose is particularly preferred because of its low glass transition point and its properties as a "water substitute" in the stabilization of proteins.

The sample extraction buffer may preferably contain one or more adjuvants selected from water-soluble dyes, pH indicator, redox indicator, rottenness indicator, methylene blue, malachite green, flavourings, citronellal, geraniol. The extraction buffer may also contain a superplasticizer selected from polycarboxylate, polycarboxylate ether, naphthalene sulfonate, melamine sulfonate, lignin sulfonate.

A known sample extraction buffer is applied to a support, i.e. a sheet with good capillary and spreading properties, so that it dries rapidly on the sheet under ambient conditions. An advantageous sheet for preservation drying of the sample extract is especially a sheet made of fibers joined together to form a nonwoven or a carrier on which fibers are supported. The fabric or fleece is preferably connected to a larger area of absorbent material via two or more connecting elements (bridges) or webs. This defines the amount of sample extract absorbed. The amount of dried sample extract then results from the drying area of the sheet. This is preferably between 0.3 and 3.0 square centimetres, preferably between 0.5 and 2.0 $cm^2$, highly preferred approx. 0.78 $cm^2$ (circular area with a diameter of 1.0 cm).

The fecal sample is extracted according to the invention, depending on the analyte, with 10 to 5000 parts of sample extraction buffer. The use of 50 to 250 parts of extraction buffer is particularly advantageous in order to standardize further the running properties on the surface structure. Since the matrix of the fecal sample may contain indigestible fibres and other undigestable solid components, the extract can be filtered before application, e.g. through a sieve filter, or the solid components can be centrifuged off. The sieve filter can be located in the tip of the sampling system.

Another aspect of the instant disclosure concerns a test kit comprising a stool collection system for the collection of a known amount of fecal sample in a sample extraction buffer as described above and an area-measured material having capillary properties as described above for the collection, drying and transport of a dried sample extract. Surface and fiber material as well as sample extraction buffers are preferably designed for the determination of the following parameters from feces or stool: albumin, anti-gliadin sIgA, α1-Antitrypsin, calprotectin, ß-defensins (HBD-1, -2, -3, -5, -6), dopamine, anti-humane-tissue transglutaminase sIgA, EDN (eosinophil-derived neurotoxin), bile acids, hemoglobin, hemoglobin/haptoglobin complex, histamine, *H. pylori* antigen, ferritin, lysozyme, lactoferrin, myelo-peroxidase, pancreatic elastase, pancreatic amylase, prealbumin/transthyretin, serotonin, zonulin.

The invention and its advantages will now be described in more detail with respect to representative examples, embodiments and drawings. These are meant for illustration and description. However, the disclosure is not limited to these, but the desired scope of protection can be inferred from the attached claims.

BRIEF DESCRIPTION OF THE DRAWINGS

It is shown in.

DETAILED DESCRIPTION OF THE INVENTION

The disclosed preanalytics for quantitative analysis of fecal samples comprise the collection and transfer of a defined amount of sample into a vessel with extraction medium, a disolution or extraction of the analyte which is to be quantified from the sample matrix, for example by dispersion of the sample in the extraction buffer optionally, a separation of the extract with the analyte from the solid parts of the test and sample matrix, for example by passing the extract through a sieve filter, sedimentation or centrifugation; an application of a known amount of extract to a predetermined area with capillary and chromatographic properties, so that the sample extract can spread over the surface and dry under normal ambient conditions. This can be done by applying a predetermined number of drops to the drying area. Drying of the sample extract on the area under ambient conditions, after which the carrier with the dried sample extract represents a stable storage and transport form. The drying area is preferably punched into a larger area and connected to it via one or more webs or support elements. Excess liquid can thus flow off into the surrounding surface or will be sucked off into it. The specified drying area can then be broken out of the surrounding area for further analysis. This standardizes the amount of applied sample liquid. This also results from the viscosity and fluidity of the extraction buffer on the drying area. Viscosity and fluidity of the extract can be adjusted by the sugar concentration in the extraction buffer. The drying surface with the carrier material is preferably attached to a small wrap or envelope. This can be pre-labelled or prepared for labelling. After application and drying of the extraction buffer on the drying area, the preanalytical steps are complete.

The preanalytics are characterized by the fact that the extraction means contains a ketocarboxylic acid which can form coordination salts with amino acids and proteins to substitute respective coordinated hydrogen bonds. It was found that proteins and amino acid-like compounds will not fully denature in the presence of ketocarboxylic acids even after drying on a carrier or a drying area. The compounds are bound instead to the surface by hydrophobic interactions while remaining quantitatively soluble, being soluble and extractable even after drying.

Following preanalytical conditioning of the fecal samples (Feces, excrement, cloaca or stool), the method comprises the steps for quantitative determination of the analyte, namely elution of the analyte from the drying area into a known amount of test buffer; optionally separating the carrier material from the test buffer, and quantitative determination of the analyte by an enzymatic or immunological reaction.

The aqueous extraction solution of the fecal sample contains in molar excess, based on the extracted proteins and analytes, preferably 1 to 50 mM/L ketocarboxylic acid with 1 to 12 carbon atoms, which can form water-soluble coordinated hydrated salts with amino acid-containing compounds, and buffer salts for a pH between 3 and 10. Detergents, solubilizing agents, complexing agents, redox agents, biocides, adjuvants and salts for the adjustment of ionic strength may optionally be added.

The keto carboxylic acids are preferably selected from the group consisting of α-keto monocarboxylic acids, α-keto dicarboxylic acids, β-ketocarboxylic acids, β-keto dicarboxylic acids, α-keto propionic acid (pyruvic acid), acetoacetic acid, ketomalonic acid (mesoxalic acid), oxaloacetic acid, oxal succinic acid, α-keto glutaric acid, isocitrate, oxohexanoic acid (ketocaproic acid), oxoheptanoic acid (ketoenanthic acid), Y-keto carboxylic acids, levulinic acid, phenylpyruvic acid, ketone derivatives and esters of terephthalic acid, as well as mono- or diesters of the above-mentioned ketocarboxylic acids with a linear or branched alcohol having 1 to 6 carbon atoms, glyoxylic acid, glyoxylic acid ethyl ester, pyruvic acid ethyl ester.

The extraction buffer may contain one or more preserving sugars which can form hydrate-like salts when drying the buffer with the proteins. They will not crystallize on the carrier at room temperature but become glassy. The extraction buffer may contain mono, di- or trisaccharides such as sucrose, lactose, maltose or trehalose and raffinose as trisaccharide. Preferred are sucrose, lactose, maltose or especially trehalose. The extraction buffer may also contain amino sugars, i.e. monosaccharides which have a primary, secondary or tertiary amino group or an acylated amino group (—NH—CO—R) instead of a hydroxy group. Glucosamine, N-methylglucosamine, galactosamine and neuraminic acid are preferred. The sugar/amino sugar is present in the preparation of the extraction buffer preferably in an amount so that after drying and re-elution from the carrier in the intended volume of test buffer it is present in the solution in a concentration of about 1 to 200 mg/ml. The preferred concentration of the sugar in the test buffer is 30 to 50 mg/ml. The extraction buffer can therefore contain 0.001 to 5.0 percent by weight, based on the total weight, preferably 0.005 to 0.5 percent by weight sugar and/or amino sugar. Trehalose is particularly preferred. Although trehalose is slightly hygroscopic, it has a comparatively high gelling and glass transition point. The glass transition describes the temperature range in which an amorphous substance passes from the solid glass-like region to the viscoelastic, "rubber-like" region. This area plays an essential role in the encapsulation of substances in amorphous carbohydrate-containing matrices such as cellulose fibers. Trehalose in nature protects cells from injury by ice crystals during frost or freezing processes and also during drought. In a way, trehalose is functionally similar to sucrose, but has different glass point and stabilizing properties. Trehalose occurs naturally in plants and fungi and in the haemolymph of many insects. Trehalose is chemically, thermally and acid stable and rapidly soluble in water. Trehalose is less soluble at low temperatures and more soluble than sucrose at high temperatures. Unlike disaccharides, trehalose is not hydrolyzable and cannot participate in a Maillard reaction with amino acids or proteins. Another advantage is that it has a high adhesive strength on many plastics and on cellulose and thus prevents the dried sample extract from crumbling off the surface of the carrier during transport.

The extraction buffer may contain one or more adjuvants selected from water-soluble dyes, pH indicator, redox indicator, rottenness indicator, methylene blue, malachite green, flavouring, citronellal, geraniol. The extraction buffer may also contain a superplasticizer selected from polycarboxylate, polycarboxylate ether, naphthalene sulfonate, melamine sulfonate, lignin sulfonate.

The fecal sample is extracted, depending on the analyte, with 10 to 5000 parts of sample extraction buffer. The use of 50 to 250 parts of extraction buffer is particularly advantageous in order to standardize the running properties on the area-measured material. Since the matrix of the fecal sample may contain indigestible fibres and other undigested solid components, the extract may further be filtered before application, e.g. through a sieve filter, or the solid components may also be separated off by centrifugation. The sieve filter can be located in the tip of the sample collection system.

The sample extraction buffer may be applied in a known quantity to a carrier, i.e. an area-measured material with good capillary and spreading properties, so that the fluid sample dries rapidly on the material under ambient conditions. An advantageous area-measured material for preservative drying of the sample extract is in particular a structure made of fibers joined together to form a nonwoven or a carrier supporting fibers. The area-measured material or fabric is preferably incorporated in a larger area of absorbent material via two or more connecting elements or webs. This allows a definition of the amount of sample extract which will become absorbed. The amount of dried sample extract then results from the drying area of the sheet. The drying area is preferably between 0.3 and 3.0 cm$^2$, preferably between 0.5 and 2.0 cm$^2$, highly preferred about 0.78 cm$^2$ (a circular surface of a diameter of 1.0 cm).

One aspect of the disclosure relates to a matched test set for the patient or test person comprising a stool collection system for a collection of a predetermined amount of fecal sample in a predetermined amount of sample extraction buffer, as described above, and an area-measured material having capillary properties as described above for collection, for drying and transport of the dried sample extract. The stool collection system is so designed so that the test person himself can apply a given number of defined drops of sample extract (e.g. 200 µl) onto the pre-cut drying surface. Quantities, buffers, area and fibre material as well as sample extraction buffers are preferably designed for a determination of the following parameters from feces or stool: albumin, anti-gliadin sIgA, a1-antitrypsin, calprotectin, 1-defensins (HBD-1, -2, -3, -5, -6), dopamine, anti-humane-tissue transglutaminase sIgA, EDN (eosinophil-derived neurotoxin), bile acids, hemogloblin, hemoglobin/haptoglobin complex, histamine, *H. pylori* antigen, ferritin, lysozyme, lactoferrin, myelo-peroxidase, pancreatic elastase, pancreatic amylase, prealbumin/transthyretin, serotonin, zonulin.

The quantitative determination of the analyte after its dissolution from the carrier material in the test buffer can preferably be done by means of an immunological reaction. The binding assay may be performed in an ELISA (enzyme-linked immuno-sorbens assay), RIA (radioimmunoassay), FIA (fluorescence immunoassay), LIA (luminescence immunoassay), or ILMA (immuno luminometric assay). Particularly preferred are non-radioactive detection systems based on fluorescence and chemiluminescence markers (FIA or LIA).

The application of the sample extract to a defined drying surface, i.e. a carrier with capillary action, is essential for the preanalytical conditioning. Furthermore, it is essential that the analyte or target protein on the drying surface is neither denatured nor irreversibly bound, since the analyte needs to be dissolved quantitatively again after its intermediate preservation on the drying area. When extracted form the sample matrix the analyte is dissolved first time already. The extract may optionally be separated from solids of the matrix by sedimentation, floating, filtration or centrifugation. A defined quantity of the extract is then applied to the matrix of the drying material or carrier, e.g. by way of a given number of drops. When applied to a drying surface with capillary properties the extract with its protein mixture will be subject to a partial chromatographic separation whereby the analyte is also separated from digestive enzymes. The intestinal bacteria present in the extract will be inactivated in a glassy sugar layer. The analyte, the target protein, will therefore end-up in a dry state and be protected as a soluble salt of a beta-ketocarboxylic acid on the surface and in the cavities of the carrier material.

The method requires the use of a area-measured material with good capillary and spreading properties. This is given for a nonwoven material, a fabric of fibers joined together to form a nonwoven or carrier on which fibers are supported. Directional fibres or ordered filaments produce a high capillary action and allow a spreading and drying of the extraction solution of the sample. The fibers may be selected from cellulose fibers, glass fibers, fibers of polyester, polyethersulfone (PES), polyamide (nylon), polypropylene, polytetrafluoroethylene (PTFE), polycarbonate, cellulose nitrate or cellulose acetate, and blends of these fibers. Due to the different bonding processes, the nonwoven material can also resemble paper, films or fibre-reinforced plastics. Other flat structures with good capillary and spreading properties are chromatographic thin-film plates, i.e. a foil or plate with a thin layer of a stationary separating material such as diatomaceous earth, which is then traversed by the aqueous sample extraction solution.

The area-measured material is advantageously designed for absorption and drying of 10 to 1000 µl aqueous sample extract, preferably 50 to 500 µl. The drying area can be designed so that too much extraction solution is discharged at two or more points via bridges, webs or teeth. The drying area can be part of a larger sheet and surrounded by slot and hole punching so that it can be broken out of the larger area. Many diecut patterns and structures are possible to limit the drying area. In one design, one or more drying areas the size of coins (Euro or Dollar piece) or a stamp are diecut into a larger area of non-woven material. Several defined drying areas allow several quantitative determinations of stool parameters.

The carrier with the dried sample extract is then broken out of the larger area prior to analysis or dissolution of the stool proteins. This allows precise control and standardization of the applied quantity and the applied amount of dried sample extract. The thickness of the absorbent material is such that approximately 200 to 250 µl of sample extract can be retained on a carrier having the size of a coin stamp. The dried sample extract on the carrier or fleece or fibre material represents the storage and transport form which is stable for days and weeks and which can be sent by post without major logistical constraints to the clinical laboratory for examination. If the drying carrier is encased within an envelope or shroud, hygiene problems are also solved. Odour is a problem encountered with liquid transport and liquid stabilisation conditions.

Representative examples of the preanalytics and determination are described below. However, the disclosure is not limited to the examples, but the scope of protection has been described in the claims.

EXAMPLES

Example 1—Quantitative Determination of Pancreatic Elastase in Stool

Preface:

Pancreatic elastase has a molecular weight of 26 kDa and is a serine protease. It is secreted together with other digestive enzymes by the pancreatic acinar cells as proenzyme and then activated by cleavage in the duodenum. It is bound to bile salts and is thus protected from digestion during intestinal passage. The concentration of pancreatic elastase in the stool is a measure of the secretory performance of the pancreas. The concentration determination in stool allows diagnosis of pancreas an exocrine insufficiency, a clinical determination indicated in case of unclear diarrhea, blockage, steatorrhea, flatulences, weight loss, upper abdominal pain as well as food incompatibilities. Its determination in stool also allows monitoring of the exocrine pancreas function in cases of cystic fibrosis, diabetes mellitus or chronic pancreatitis. A regular determination should be made in all these cases.

Pre-Analytic Test Kit:

A stool collection system (Immundiagnostik AG, Bensheim, DE—Article-No. K 6998SAS), wherein the tube has been filled with 1.5 ml stool extraction buffer according to the invention (20 mM $Na_2HPO_4$, 2.6 mM $KH_2PO_4$, 2.7 mM KCl, 137 mM NaCl, 50 mM ß-sodium glutarate, 20 mM trehalose, 0.1% SDS, 1% Triclosan®, methylene blue, citronellal). The amount stool that could be transferred with the stool lance was 15 milligrams as controlled by the size of the notches and dents; the dilution factor was thus 1:100. The raw stool must be transferred into the extraction buffer using the lance or pin. Any excessive stool will be compulsorily wiped off when using the transfer system. The patient is instructed to homogenously disperse the feces in the extraction buffer and drop 200 microlitres (4 drops) of "homogeneous solution" onto a round cellulose piece (Whatman, US) of 1 cm diameter using a calibrated minipipipette (Minivette® from Sarstedt, DE). The aqueous stool extract inevitably spreads on this drying area, and will quickly dry at room temperature or ambient conditions. The drying area is diecut into a larger area of cellulose fleece so that any excess of liquid extract ("the 5th drop") will be sucked-off. This dried fecal spot represents a stable transport and storage form of the specimen which can sent or returned to the clinical laboratory.

Comparative series showed that the storage of the sample on the fibre fleece was stable for four consecutive days in so far as the storage time had no substantial influence on the quantitative result. The fibre fleece can therefore be sent to the laboratory in an envelope using the postal system. Normally, the stability of pancreatic elastase in raw stool must been ensured by cooling (4-8° C.) or is limited at room temperature to less then 3 days. When frozen at −20° C. up it is stable up to one year (Stein, J. et al., *Immunoreactive elastase I: clinical evaluation of a new noninvasive test of pancreatic function*. Clinical Chemistry, 1996, 42(2):222-6; Nandhakumar, N. & Green, M. R., Interpretations: *How to use faecal elastase testing. Archives of disease in childhood. Education and Practice Edition*, 2010, 95(4):119-23]. The disadvantage of freezing is that it is associated with a freeze/thaw cycle. The advantage of the drying process is that several samples can be produced from one stool and processed separately, i.e. several parameters and markers can be examined simultaneously. Only the dilution factor for the respective parameter has to be considered.

Quantitative Determination.

The determination of the pancreatic elastase on the fibre fleece was carried out using a conventional elastase ELISA (Immundiagnostik AG, Bensheim, DE—Article No. K 6915). The drying surface with the faecal extract was separated from the fleece material and all salts on it dissolved in 1.0 ml ELISA washing buffer to obtain a "second extract". The pancreatic elastase dissolved from the fibrous fleece was bound by monoclonal anti-elastase antibodies immobilised on a microtiter plate. Unbound proteins of the second extract were rinsed off the microtiter plate in washing steps and the bound pancreatic elastase was detected with peroxidase-labelled second antibodies (mouse anti-human pancreatic elastase), the so-called antibody conjugate. After further washing steps, a solution with tetramethylbenzidine (TMB) was added to the peroxidase as substrate for a color reaction. The color development on the microtiter plate is then proportional to the amount of analyte in the sample or in the standard reference. The concentration in the sample can then be determined by comparison using the parallel standard curve. Irrespective of the initial sample and the drying time on the fibre fleece, the pancreatic elastase dissolves reproducibly and quantitatively when the described stool extraction buffer is used and can thus be determined even after its transport on the fibre fleece.

Specifically, 100 µl standard, control or "second extract" (1 ml washing buffer) was pipetted in double values onto an antibody-coated microtiter plate and incubated at room temperature for 30 minutes while shaking. The microtiter plate was washed 5 times with washing buffer and 100 µl antibody conjugate were pipetted into each well. This was followed by 30 minutes incubation at room temperature while shaking. The microtiter plate was washed several times with washing buffer, 100 µl TMP substrate was pipetted into each well followed by incubation for 15 minutes at room temperature while protected from sunlight. The color reaction was stopped by adding a stop solution (100 µl $H_2SO_4$ solution) to each well. The measurement was then performed in a photometer at a wavelength of 450 nm.

Example 2—Method Comparison Direct Determination Vs Dried Fecal Spot (DFS)

Figure 3:
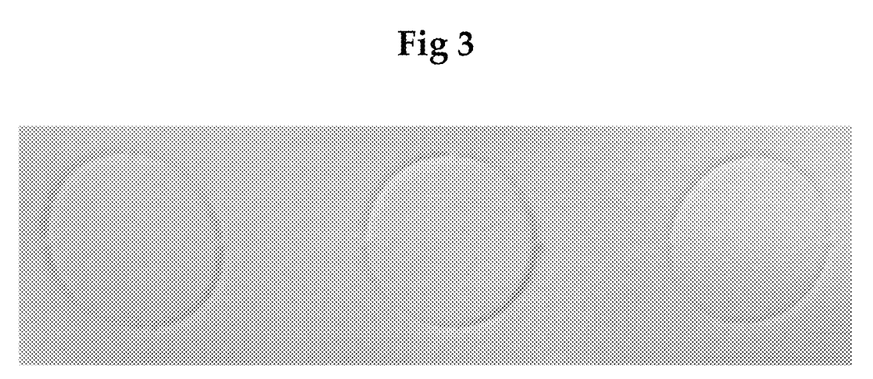
FIG. 3 a photo of a section of the area-measured material, wherein the drying area is limited by sprocket holes while in fluid connection via bridges to a larger fibrous web; the drying area can be separated out prior and for analysis.

Fecal raw samples (stored at −20° C.) were examined on their concentration of pancreatic elastase directly and after dissolving a dried fecal spot from a fibre fleece. For direct determination, 15 mg stool sample was dispersed in 1.5 ml extraction buffer (dilution 1:100) using the stool collection system (SAS) described in Example 1. The suspension was equilibrated at room temperature for 10 minutes; see FIG. 3. The first extract (dilution 1:100) was further diluted 1:100 with ELISA washing buffer to a final dilution of 1:10,000. The immunological determination of the pancreatic elastase was performed using 100 µl final dilution per cavity as in example 1.

Determination of dried fecal spots (DFS) on fibre fleece. 100 µl stool extraction buffer (dilution 1:100) was dripped onto a fibrous fleece, dried at room temperature and stored for 7 days (one week) at ambient temperature in an envelope on the shelf. The dried area were then separated from the fleece material and treated for 10 minutes each in a 1.5 ml Eppendorf tube with 1.0 ml washing buffer (dilution 1:1000) with vortexing. The fibre fleece was centrifuged and 100 µl supernatant diluted with 900 µl ELISA washing buffer (dilution 1:10.000). 100 µl of this final dilution was used in the test per well. The results of the method comparison are shown in Table 1 and graphically in FIG. 1 as a scatter-plot

TABLE 1

Method comparison between direct determination and determination after drying and dissolution from a fibre fleece for fecal pancreatic elastase

| Sample No. Conc. of fecal pancreatic elastase | Direct determination from liquid extract [µg/ml] | Determination after dissolution of the DFS from the fibre fleece [µg/ml] |
| --- | --- | --- |
| 1 | 213.6 | 204 |
| 2 | 147.5 | 156.45 |
| 3 | 167.8 | 180.3 |
| 4 | 605.5 | 406.25 |
| 5 | 155.4 | 225.55 |
| 6 | 582.2 | 458.25 |
| 7 | 340.9 | 285.05 |
| 8 | 275.4 | 244.15 |
| 9 | 662.1 | 405.55 |
| 10 | 343.2 | 270.3 |
| 11 | 356.3 | 302.1 |
| 12 | 115.5 | 136.35 |
| 13 | 182.2 | 218.6 |
| 14 | 258.4 | 251.55 |
| 15 | 271.7 | 243.75 |
| 16 | 377.5 | 299.95 |

Figure 1:
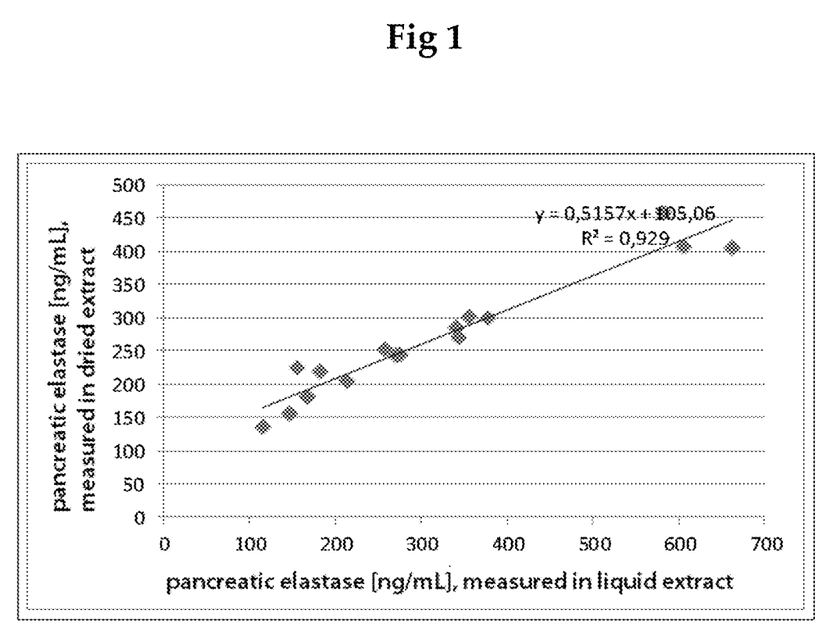
FIG. 1 a scatter-plot and the result of a method comparison between direct determination from extract fluid and determination after disolution of the dried fecal spot (DFS)
Figure 2:
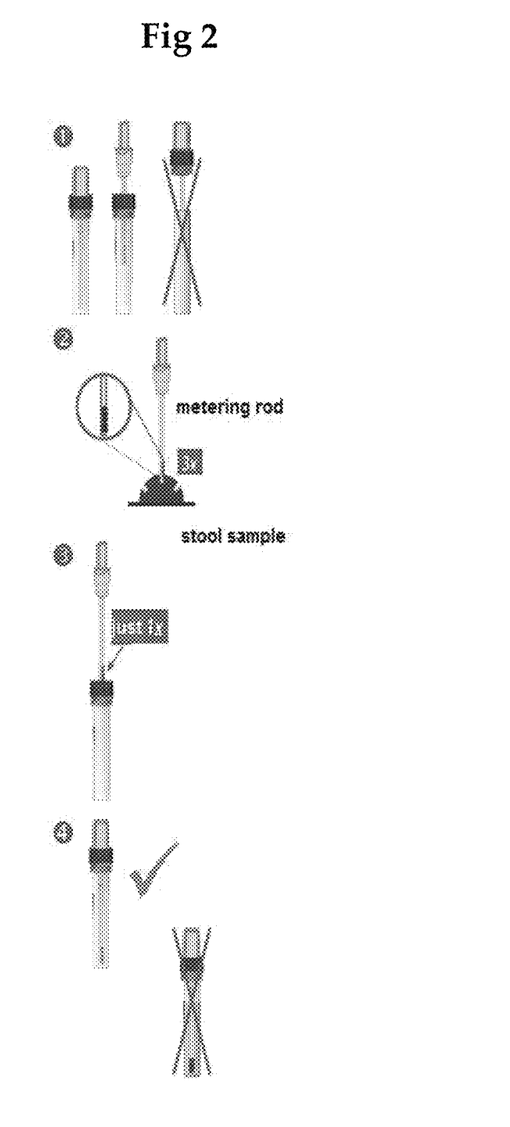
FIG. 2 a graphical representation of the stool collection system for transfer of a defined amount of stool (15 mg) into the extraction buffer (1.5 ml) according to the invention.

The correlation between these two measurement methods was very strong (R=0.96). The coefficient of determination $R^2=0.929$; FIG. 1 shows the point analysis (scatter plot). The correctness or correlation is here a measure for the deviation of a measured value from the "true" value due to a systematic error. It was proven by comparison with a validated method, the direct determination in "liquid". The methods proved to give absolute identical results.

Example 3—Comparison of the Precision of the Methods

The following precision information (intra-assay) described how much analytical values scatter with repeated analyses. The inter-assay imprecision or reproducibility was also determined. Table 2 shows the reproducibility or scattering for two samples ("11"—mean value—and "22"—high value) with 20 replicates.

TABLE 2

Scattering (n = 20) of measured values when determined from dried fecal soots

| Sample No. "11" | Sample No. "22" |
| --- | --- |
| 321.3 | 537.4 |
| 307.9 | 555 |
| 268.0 | 548.2 |
| 304.3 | 480.7 |
| 302.6 | 540.0 |
| 291.4 | 528.8 |
| 281.1 | 518.0 |
| 276.4 | 521.4 |
| 286.5 | 530.9 |
| 281.9 | 552.7 |
| 285.5 | 539.8 |
| 326.2 | 562.0 |
| 340.8 | 491.7 |
| 298.8 | 509.6 |
| 282.2 | 544.0 |

TABLE 2-continued

Scattering (n = 20) of measured values
when determined from dried fecal soots

| Sample No. "11" | Sample No. "22" |
|---|---|
| 302.7 | 530.2 |
| 289.8 | 525.8 |
| 289.4 | 494.8 |
| 298.3 | 501.1 |
| 297.9 | 512.8 |

The standard deviation (n=20) was 17.25 µg/ml for a raw sample "11" with a mid-high pancreatic elastase concentration (MW=[296.65 µg/ml]). The coefficient of variation was 5.81 percent. The standard deviation was 21.89 for a raw sample "22" with a high pancreatic elastase concentration (MW=526.25 [µg/ml]).

The inter-assay imprecision or reproducibility of the determination of fecal pancreatic elastase concentration on different days was determined for determinations from dried fecal spot (DFS) and for direct determinations from fecal extraction fluids.

TABLE 3

Imprecision of determination methods (n = 20) using samples
of liquid stool extract (SES) and dried fecal spots (DFS)

| Date | Sample "14" SES | Sample "14" DFS | Sample "15" SAS |
|---|---|---|---|
| 161031_1 | 206 | 201 | 304 |
|  | 192 | 205 | 314 |
| 161031_2 | 166 | 213 | 317 |
|  | 166 | 215 | 321 |
| 161101_1 | 234 | 215 | 312 |
|  | 230 | 202 | 300 |
| 161101_2 | 216 | 245 | 342 |
|  | 226 | 244 | 320 |
| 161102_1 | 217 | 231 | 306 |
|  | 208 | 227 | 306 |
| 161102_2 | 241 | 211 | 325 |
|  | 234 | 216 | 307 |
| 161104-1 | 254 | 295 | 339 |
|  | 248 | 300 | 368 |
| 161104_2 | 206 | 208 | 342 |
|  | 256 | 197 | 365 |
| 161110_1 | 238 | 232 | 364 |
|  | 243 | 230 | 363 |
| 161110_2 | 257 | 231 | 366 |
|  | 254 | 257 | 340 |
| Number | 20 | 20 | 20 |
| MV (µg/mL) | 224.60 | 228.75 | 331.05 |
| STABWNs | 26.77 | 27.73 | 23.31 |
| VK [%] | 11.92% | 12.12% | 7.04% |

The results show that precision and reproducibility are not substantially affected by the drying of the stool extract on a fibrous fleece. Thus, the preanalytical procedure provides a high practical value because it solves the problems with the transport and stability of stool samples.

Example 4—Determination of Calprotectin from Dried Fecal Spots (DFS)

Fecal calprotectin is a marker with high negative predictive power with respect to gastrointestinal diseases. If the calprotectin level in the stool is low, there is a high probability that there is no organ disease of the intestinal tract. This is important for a differentiation between patients with irritable bowel disease and those with chronic inflammatory bowel disease (CED). Detection from stool by ELISA or turbidimetric ELISA from a liquid stool extract correlates well with histological and endoscopic findings of disease activity in Crohn's disease and ulcerative colitis, as well as with standard reference for CED activity, the measurement of fecal excretion of 111-indium-labelled neutrophil granulocytes. However, the granulocyte test is very time-consuming (hospital stay, isotope determination and disposal) and stressful. Calprotectin in stool is an ideal monitoring marker for Crohn's disease or after polyp ablation. Initial experiments have shown that dried fecal spots can be used to determine immunologically the concentration of calprotectin in stool. The determination of calprotectin is analogous to example 1. The method comparison (DFS vs liquid extract) showed a high correlation of measured values (R=0.95); the adjusted coefficient of determination R2 was 0.918.

Example 5—Determination of Occult Blood from Dried Fecal Spots (DFS)

The detection of haemoglobin in stool is a useful marker for gastrointestinal bleedings and for colorectal cancer screening. Blood in stool may come from tumors or polyps in the intestine. Other possible indications include Crohn's disease, ulcerative colitis, etc. If haemoglobin can be detected in the stool, a colonoscopy must be performed to determine where the bleedings originate and whether there is a tumour or a precursor thereof in the intestine. In combination with colonoscopy, the immunoassay for fecal Hb has been shown to reduce the mortality risk of colon cancer. Sampling and quantitative determination can be performed as in example 1. A particular advantage is a high sample stability at room temperature. Hemoglobin is degraded by 50% in stool at room temperature so that the raw stool must be frozen preanalytically. Even in a stabilization buffer, the degradation of occult hemoglobin at room temperature still amounts to approx. 3 to 7% per day, often even more. If, on the other hand, stool is preserved as a dried fecal spot on a fleece, as in example 1, the haemoglobin is quantitatively stable for weeks and the sample can be sent using the postal system to a laboratory for analysis. Since small amounts of blood are regularly excreted with the stool, the determination for occult hemoglobin must be quantitative, not only analytical. Since the stool sample is stable with regard to occult blood in the stool, a threshold value can determined when a colonoscopy is indicated. As with other tests in this field, this threshold value must also be optimized for the desired sensitivity and specificity (see Gies A et al, Direct Comparison of Diagnostic Performance of 9 Quantitative Fecal Immunochemical Tests for Colorectal Cancer Screening, Gastroenterology, 2018, 154:93-104).

The invention claimed is:

1. A preanalytical method of sample preparation, the sample comprising feces, excrement or stool, for quantitative determination of a proteinaceous analyte, comprising the steps:
(a) collecting the sample and transferring a known amount into a prepared vessel containing a known amount of aqueous extraction solution; (b) dispersing and extracting the proteinaceous analyte from the sample matrix;
(c) separating the aqueous extract from the solid matrix components and applying a known volume of aqueous extract to a dry support material having capillary properties and chromatographic properties such that the extract runs and spreads on the support material;

(d) drying the support material at ambient temperature, wherein the support with the dried extract is a preservation and transport form;
(e) elution of the proteinaceous analyte from the carrier material into a known amount of assay buffer;
(f) optionally separating the carrier material from the assay buffer; and
(g) quantitatively determining the analyte,
characterized in that the aqueous sample extraction solution contains an excess of 0.001 to 5.0% by weight of ketocarboxylic acid having 1 to 12 carbon atoms which, under ambient conditions, form water-soluble hydrated salts with amino acids and proteins, as well as conventional buffer salts, detergents, solubilizing agents, complexing agents, biocides, adjuvants and salts for adjusting ionic strength.

2. The preanalytical method according to claim 1, wherein the ketocarboxylic acids are selected from the group consisting of α-keto monocarboxylic acids, α-keto dicarboxylic acids, β-keto-carboxylic acids, β-ketodicarboxylic acids, ketopropionic acid (pyruvic acid), acetoacetic acid, ketomalonic acid (mesoxalic acid), oxaloacetic acid, oxalsuccinic acid, α-keto glutaric acid, isocitrate, oxohexanoic acid (keto-caproic acid), oxoheptanoic acid (ketoenanthic acid), Y-keto carboxylic acids, levulinic acid, phenylpyruvic acid, ketone derivatives and esters of terephthalic acid, and mono- or diesters of the abovementioned ketocarboxylic acids with a linear or branched alcohol having 1 to 6 carbon atoms, glyoxylic acid, glyoxylic acid ethyl ester, pyruvic acid ethyl ester.

3. The method according to claim 1, wherein the extraction buffer contains 0.001 to 10.0 wt. % of one or more saccharides selected from preservative saccharides, trehalose, sucrose, maltose, based on the total weight of the composition, preferably 0.005 to 0.5 wt. %.

4. The method according to claim 1, wherein the extraction buffer contains one or more additives selected from water-soluble dyes, pH indicator, redox indicator, decay indicator, methylene blue, malachite green, flavourings, citronellal, geraniol.

5. The method according to claim 1, wherein the carrier comprises fibers selected from cellulose fiber, glass fiber or fibers of polyesters, polyethersulfone (PES), polyamide (nylon), polypropylene, polytetrafluoroethylene (PTFE), polycarbonate, cellulose nitrate or cellulose acetate.

6. The method according to claim 1, wherein the extraction buffer contains a plasticizer selected from polycarboxylate, polycarboxylate ether, naphthalene sulfonate, melamine sulfonate, lignin sulfonate.

7. The method according to claim 1, which comprises extracting a portion of a sample matrix comprising 50 to 250 parts, preferably 80 to 120 parts, of extraction buffer.

8. The method according to claim 1, wherein the solid support is designed for a defined uptake and for drying from 100 to 250 µl aqueous extract and any excess aqueous extraction solution is removed so that the analyte contained therein is excluded from the quantitative determination.

9. The method according to claim 1 for the quantitative determination of the fecal content of calprotectin (S100A8/S100A9; MRP8(MRP14)); pancreatic elastase, histamine, lactoferrin, beta-defensins (HBD-1, -2, -3, -5, -6), EDN, (eosinophil-derived neurotoxin), hemoglobin, hemoglobin/haptoglobin complex.

10. A test kit comprising a stool collection system having a known amount of sample extraction buffer according to claim 1 and a solid support for the collection, preservation and transport of a known amount of dried extract,
wherein the solid support is designed for a defined uptake and for drying from 100 to 250 µl aqueous extract and any excess aqueous extraction solution is removed so that the analyte contained therein is excluded from the quantitative determination, and
optionally the ketocarboxylic acids are selected from the group consisting of α-keto monocarboxylic acids, α-keto dicarboxylic acids, β-keto-carboxylic acids, β-ketodicarboxylic acids, ketopropionic acid (pyruvic acid), acetoacetic acid, ketomalonic acid (mesoxalic acid), oxaloacetic acid, oxalsuccinic acid, α-keto glutaric acid, isocitrate, oxohexanoic acid (keto-caproic acid), oxoheptanoic acid (ketoenanthic acid), Y-keto carboxylic acids, levulinic acid, phenylpyruvic acid, ketone derivatives and esters of terephthalic acid, and mono- or diesters of the abovementioned ketocarboxylic acids with a linear or branched alcohol having 1 to 6 carbon atoms, glyoxylic acid, glyoxylic acid ethyl ester, pyruvic acid ethyl ester.

11. The test kit according to claim 10, wherein the carrier is bonded to a major amount of absorbent fibrous material via one or more defined webs so that excess liquid is drained from the carrier.

12. The test kit according to claim 10 designed to determine the fecal content of calprotectin (S100A8/S100A9; MRP8(MRP14)); pancreatic elastase, histamine, lactoferrin, beta-defensin (HBD-1, -2, -3, -5, -6), EDN (eosinophil-derived neurotoxin), haemogloblin, haemoglobin/¬haptoglobin complex.

* * * * *